(12) United States Patent
Debroche et al.

(10) Patent No.: US 7,501,639 B2
(45) Date of Patent: Mar. 10, 2009

(54) OPTICAL DEVICE FOR LIGHT DETECTOR

(75) Inventors: Claude Debroche, Cebazat (FR); Hervé Crespeau, Paris (FR); Bruno De Vandiere, Clermont-Ferrand (FR)

(73) Assignee: Flowgene, Saint-Beauzire (FR)

( * ) Notice: Subject to any disclaimer, the term of this patent is extended or adjusted under 35 U.S.C. 154(b) by 0 days.

(21) Appl. No.: 10/596,340

(22) PCT Filed: Dec. 10, 2004

(86) PCT No.: PCT/FR2004/050678

§ 371 (c)(1),
(2), (4) Date: Aug. 8, 2006

(87) PCT Pub. No.: WO2005/059523

PCT Pub. Date: Jun. 30, 2005

(65) Prior Publication Data

US 2007/0085023 A1 Apr. 19, 2007

(51) Int. Cl.
*G01N 21/64* (2006.01)
(52) U.S. Cl. .................................. 250/458.1
(58) Field of Classification Search ........................ None
See application file for complete search history.

(56) References Cited

U.S. PATENT DOCUMENTS

| | | | |
|---|---|---|---|
| 3,946,239 A | 3/1976 | Salzman et al. | |
| 4,548,498 A | 10/1985 | Folestad et al. | |
| 4,675,300 A | 6/1987 | Zare et al. | |
| 4,871,249 A | 10/1989 | Watson | |
| 5,127,729 A * | 7/1992 | Oetliker et al. | 356/317 |
| 5,430,541 A | 7/1995 | Sapp et al. | |
| 5,895,920 A | 4/1999 | Carlsson | |
| 5,926,271 A | 7/1999 | Couderc et al. | |

* cited by examiner

*Primary Examiner*—Constantine Hannaher
(74) *Attorney, Agent, or Firm*—Pearne & Gordon LLP

(57) ABSTRACT

An optical device (1) includes a cavity (2) for which at least part is ellipsoidal with a first focus ($F_1$) and a second focus ($F_2$). The device includes means of presenting a medium containing components to be analyzed in the cavity at the first focus, and the device also includes means of transporting an excitation light beam in the cavity along a path also passing through the first focus ($F_1$) to illuminate the medium at the first focus. The ellipsoidal part of the cavity includes a wall reflecting light emitted by the medium in response to the excitation light beam, and the device includes means (5) of collecting said emitted light at the second focus ($F_2$).

21 Claims, 4 Drawing Sheets

OPTICAL DEVICE FOR LIGHT DETECTOR

TECHNICAL FIELD

This invention relates to an optical device for collecting light emitted by constituents of a fluid or a gas under the action of an incident light beam. It is particularly applicable to detection of components circulating in a tube.

STATE OF PRIOR ART

In analytical chemistry, analysis of components in a liquid or a gas uses a number of techniques including separation techniques such as High Performance Liquid Chromatography or capillary electrophoresis, in association with a detector. This liquid or this gas circulates in a tube, and the purpose of the detector is to identify one or several constituents of this liquid or gas.

All light detectors operate on the same principle; an incident light beam illuminates the tube and light emitted or transmitted by the component to be detected is collected in one direction. The performance of a detector is related to its capability of identifying one or more components in a liquid or a gas. It is usually measured in terms of sensitivity. Those skilled in the art inject different concentrations of a product into the detector, and the detection limit corresponds to the lowest concentration of the product that the detector is capable of identifying. The objective of a detector is to present the highest possible detection performances.

U.S. Pat. No. 4,548,498 divulges a device for detection of fluorescence induced by a laser beam for use in liquid chromatography. A laser beam is directed onto a liquid flow. Fluorescence light emitted by the liquid at an illumination point is directed to a measurement device through a mirror.

U.S. Pat. No. 4,675,300 divulges a device for detection of fluorescence light provoked by laser excitation of a liquid being studied. Fluorescence light emanating from the liquid under laser excitation is collected by an optical fibre.

U.S. Pat. No. 5,926,271 divulges a detector of fluorescence induced by a laser beam. The detector comprises a means of emitting a laser beam, a cell formed inside a capillary, the cell receiving a solute containing at least one unknown substance that is fluorescent at the wavelength of the laser, illumination means including a lens with a small digital aperture, a ball-shaped lens, the same optical means collecting emitted fluorescence that is processed to provide the results of the analysis. The ball-shaped lens converts the laser beam into a divergent beam to illuminate a large volume of the cell.

One important weakness of light detectors according to known art is that only part of the fluorescence light is collected, which reduces detection performances of detectors.

PRESENTATION OF THE INVENTION

The invention overcomes the disadvantages of prior art by proposing a device for collecting practically all light emitted in response to an excitation light beam.

The subject of the invention is an optical device including a cavity for which at least part is ellipsoidal with a first focus and a second focus, the device including means of presenting a medium containing components to be analysed in the cavity at the first focus, the device also including means of transporting an excitation light beam in the cavity along a path also passing through the first focus to illuminate said medium at the first focus, said ellipsoidal part of the cavity including a wall reflecting light emitted by said medium in response to the excitation light beam, the device including means of collecting said emitted light at the second focus.

The invention thus eliminates one of the disadvantages of prior art, that is that the excitation point and the collection point of emitted light are coincident. The optical device according to the invention separates these points. Since the device surrounds the excitation point, it enables volumetric collection of emitted light and its collection efficiency is very much greater than systems based on collection of light along an axis.

According to one variant embodiment, the means used to present said medium are capable of making the medium circulate along a path passing through the first focus. The path of the means used to circulate a medium and the path of the means used to transport an excitation beam may be orthogonal to each other at the first focus. The angle between the path of the means used to circulate the medium and the path of the means used to transport an excitation beam is less than 90° at the first focus.

The path of the means used to circulate the medium and the path of the means used to transport an excitation beam may both be perpendicular to the axis of the ellipsoid corresponding to the ellipsoidal shape.

The means used to circulate the medium may include a transparent tube, at least at the first focus. According to another embodiment, they may include an injector tube of the medium with one end located at the first focus and a collector tube of said medium with one end located at the other side of the first focus so that the fluid is directly subjected to the excitation light beam. The device can then be provided with orifices through which the tube or injector tube and the collector tube can pass.

The device may be provided with an inlet orifice of the excitation light beam and possibly an outlet orifice of the excitation light beam.

According to another variant embodiment, the means of presenting said medium include a case matching the shape of said part and wherein said medium can be housed at the first focus. If the case is transparent, the reflecting wall is the wall of said part. The case may also be made of a material forming said reflecting wall.

According to another variant embodiment, the means of presenting said medium include a support including said medium and that can be inserted in the optical device to present said medium at the first focus. The support may include at least one housing to contain said medium. It may include at least one channel internal to the support to transport said medium to the first focus, in a transparent part of the support. This support may be a lab on a chip.

Depending on the case, the cavity may be completely filled with a substance transparent to the excitation light beam and to said emitted light, the means for collecting emitted light comprising an opening provided with a concave lens concave towards the outside of the device, for which the focal point coincides with the second focus located outside the optical device, and the axis of which is the axis of the ellipsoid corresponding to the ellipsoidal shape, the emitted light thus not passing through any air layer before coming out of the concave lens.

The emitted light collection means may include an opening to allow light collected at the second focus to pass through. They may thus include an opening equipped with a lens or a group of lenses, the axis of which is the axis of the ellipsoid corresponding to the ellipsoidal shape and for which the focal point coincides with the second focus. The lens or group of lenses may be placed in a reception housing of the device and may be fixed to the device by a support element.

The device may consist of at least two assembled parts. One of the parts may include the ellipsoidal part, the shape of the other part may be chosen from among spherical, paraboloid, hyperboloid and ellipsoid shapes, to complete the cavity. It may be made of a metallic material. It may also be made of a plastic material, the reflecting wall of the cavity being formed of a metallic material. Advantageously, the metallic material absorbs light at the wavelength of the excitation light beam and reflects light at the wavelength of the emitted light.

BRIEF DESCRIPTION OF THE DRAWINGS

The invention will be better understood and other advantages and special features will appear after reading the following description given as a non-limitative example accompanied by appended drawings, wherein.

DETAILED PRESENTATION OF PARTICULAR EMBODIMENTS

Figure 1:
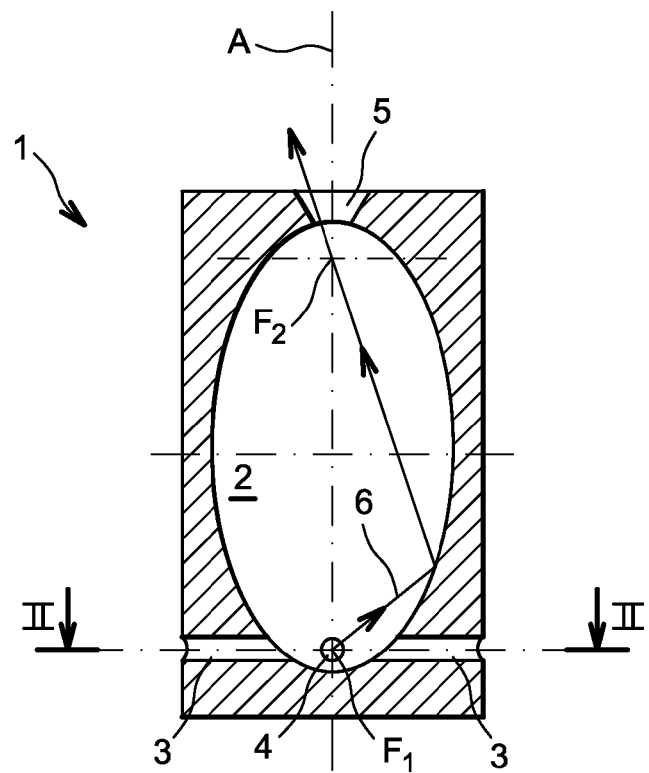
FIG. 1 is a sectional view diagrammatically showing an optical device for a light detector according to the invention.

FIG. 1 is a longitudinal sectional view diagrammatically illustrating an optical device 1 to detect light according to the invention.

The device 1 may for example be made of a metallic material such as aluminium. It includes a practically closed internal cavity 2. The cavity 2 is shaped like an ellipsoid of revolution characterised by a first focus $F_1$, a second focus $F_2$ and an axis of revolution A. Two holes 3 and 4 pass through the device at the first focus $F_1$, and intersect at the first focus $F_1$. An excitation light beam, for example a laser beam, will pass through the hole 3. A medium (liquid or gas) to be analysed will pass through the hole 4, the fluid possibly being transported inside a tube. The device 1 is provided with an opening 5 at the second focus $F_2$.

It is assumed that a fluid containing components to be identified transits to the first focus $F_1$ after passing through the hole 4. At the first focus $F_1$, the fluid is excited by a light beam passing through the hole 3. The components to be identified emit light inside the cavity 2 in response to the excitation beam.

The principle of the optical device according to the invention is based on one of the properties of the ellipse: when two rays, each from one of the two focuses of the ellipse, intersect at a point on the ellipse, the angles of incidence of these two rays at the contact point are symmetrical. Consequently, a light beam 6 emitted from the first focus $F_1$ necessarily passes through the second focus $F_2$, after reflection on the wall of the cavity. This reflected beam can then be collected through the opening 5, possibly after several reflections on the wall of the cavity 2. Note that some light beams can exit through the orifice 5 directly; this is the case for light emitted immediately adjacent to the axis A.

The holes 3 and 4 intersecting at the first focus $F_1$ may both be orthogonal to the axis A of the ellipsoid. They may also be orthogonal to each other or form a determined angle with each other.

Figure 2:
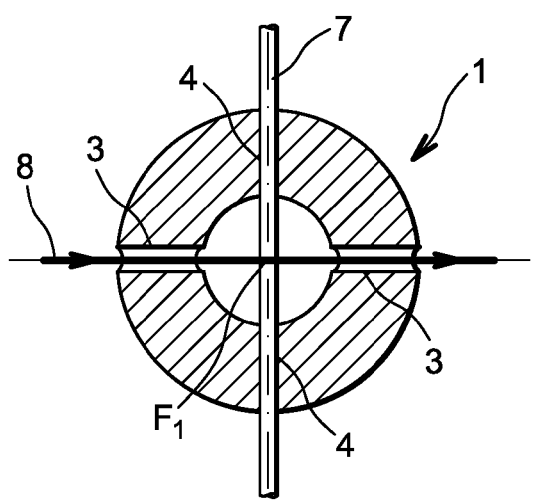
FIG. 2 is a sectional view along axis II-II in FIG. 1.

FIG. 2 is a sectional view along axis II-II in FIG. 1 including a few elements necessary for operation of the optical device. In this example embodiment, the holes 3 and 4 intersect orthogonally. The hole 4 enables passage of a transparent tube 7 transporting the medium to be analysed. A light beam 8 that excites the medium to be analysed passes through the hole 3, at the first focus $F_1$. In the example shown, the excitation light beam is output from the device through the other part of the hole 3.

Figure 3:
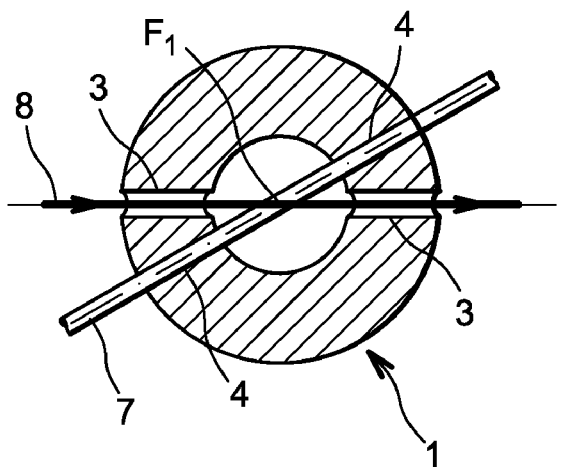
FIG. 3 shows a variant embodiment corresponding to the sectional view along axis II-II in FIG. 1.

FIG. 3 is another sectional view corresponding to axis II-II in FIG. 1 but with a few modifications. In this example embodiment, the holes 3 and 4 are still orthogonal to the axis of symmetry A, but they are no longer orthogonal to each other. The axis of the hole 3 and the axis of the hole 4 may then make an angle between them such that reflections of light emitted by the fluid and that reach the transparent material of the tube 7 are concentrated at a particular location. This particular location may be one of the parts of the hole 4 used for the tube 7 to pass through. This may be the inlet of a duct 9 placed on one of the parts of the hole 4. It may also be the association of one of the parts of the hole 4 and the inlet of a duct 9.

Figure 4:
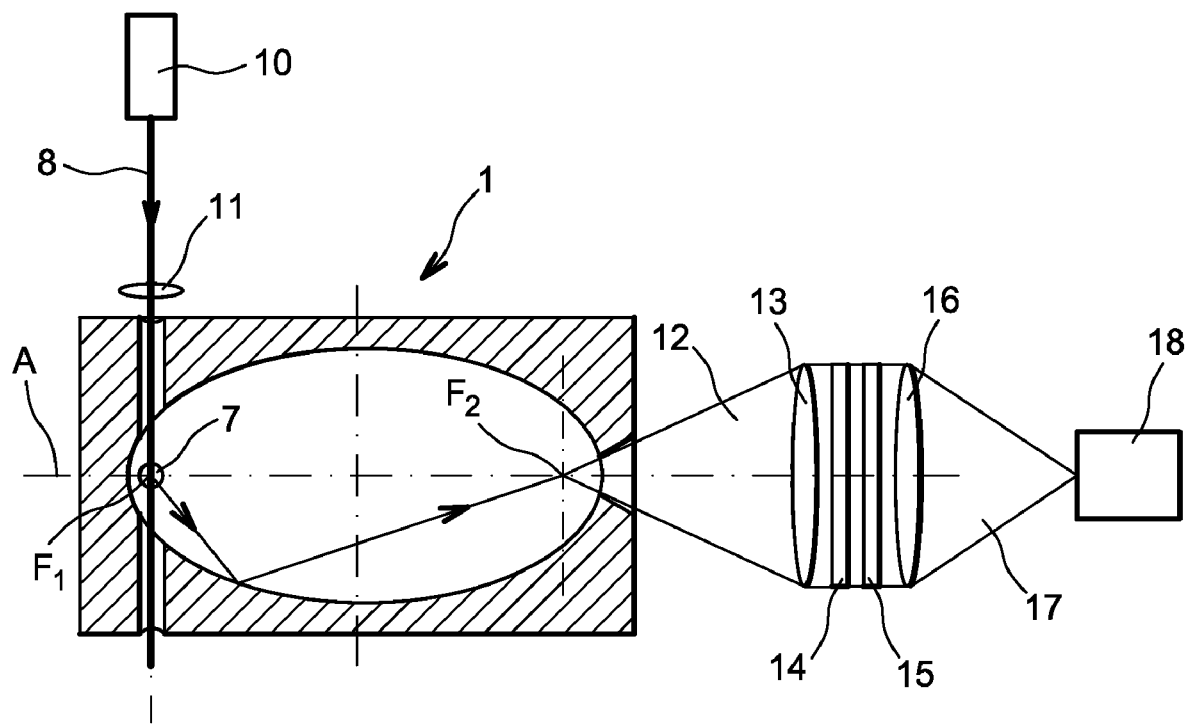
FIG. 4 diagrammatically shows use of the optical device according to the invention, for a laser-induced fluorescence detector, the detector including two lenses and two optical filters.

FIG. 4 diagrammatically shows one possible use of the optical device according to the invention. This figure clearly shows the optical device 1 according to the invention with its axis A, it first focus $F_1$ and its second focus $F_2$. The excitation light beam 8 is emitted by a laser 10 and is focused on the first focus $F_1$ by a focusing lens 11. The fluid circulating in the tube 7 is subjected to the excitation beam 8 emitted at the first focus $F_1$. Light emitted in response to the excitation light beam is collected through opening 5 as it exits from the second focus $F_2$. Collected light output from the optical device 1 forms a divergent beam 12 that is treated by an assembly including a series consisting of a collection lens 13 outputting a parallel light beam, a Notch filter 14, a high-pass type optical filter 15 and a focusing lens 16. This assembly focuses a filtered light beam 17 onto a reception element, for example a photomultiplier tube 18.

Figure 5:
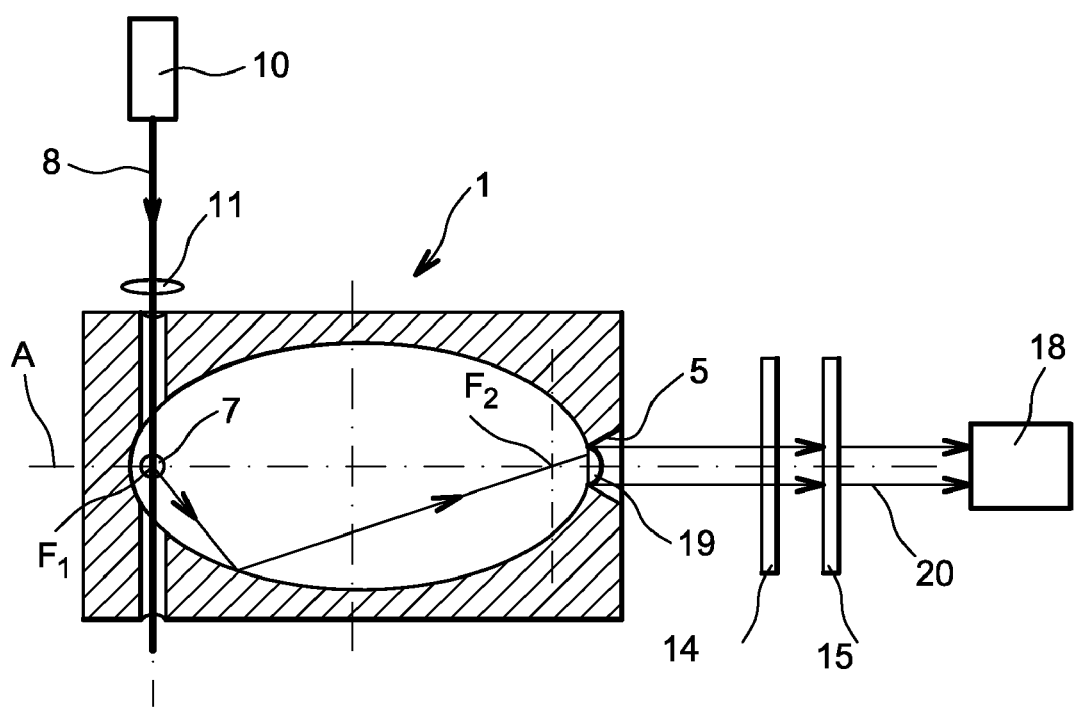
FIG. 5 diagrammatically shows use of the optical device according to the invention, for a laser induced fluorescence detector, the detector including one lens and two optical filters.

FIG. 5 diagrammatically shows another possible use of the optical device according to the invention. The same references as in FIG. 4 represent the same elements. In this example, the optical device 1 is equipped with a collection lens 19 at the opening 5, for which the optical axis is coincident with the axis of revolution A and for which the focal point coincides with the second focus $F_2$. The collection lens 18 outputs a parallel beam 20 that is filtered using a Notch filter 14 and a high-pass optical filter 15, and then reaches the photomultiplier tube 18.

Figure 6:
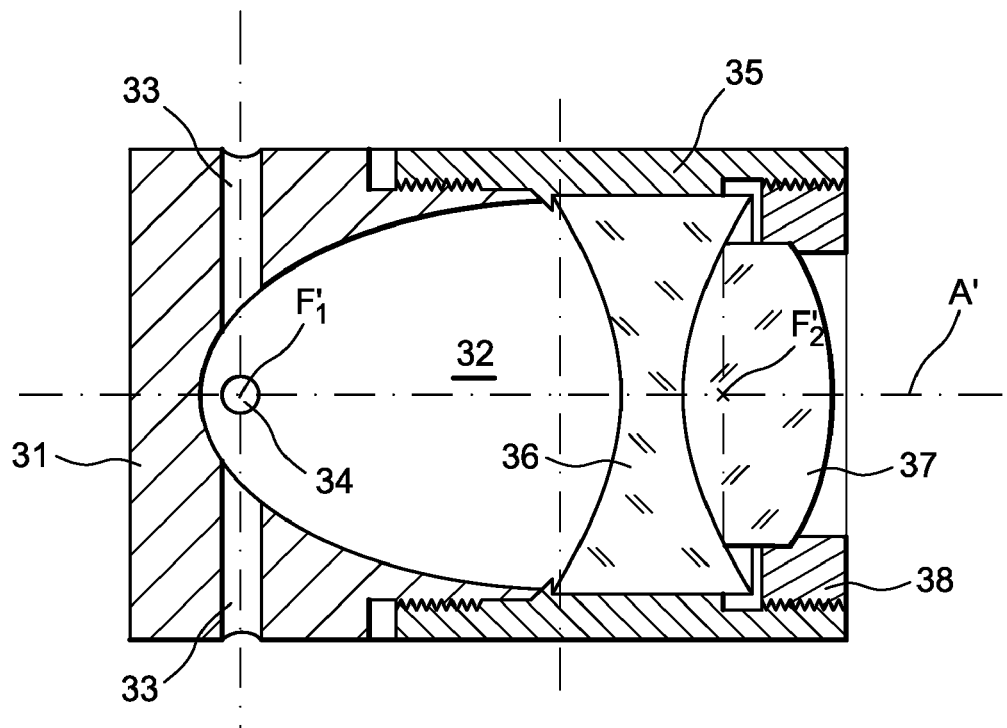
FIG. 6 is a longitudinal sectional view of an optical device according to this invention.

FIG. 6 shows a longitudinal sectional view of a more specific version of an optical device according to this invention. The device includes a first generally cylindrical part 31, for example made of aluminium, with a cavity 32 that has an incomplete ellipsoid shape. The ellipsoid shape forms a first focus $F'_1$ and a second focus $F'_2$ on the axis of symmetry A'. The first part 31 comprises a hole 33 through which an excitation light beam will pass, passing through the first focus $F'_1$ orthogonal to the axis A'. It also comprises a hole 34 through which a tube carrying a fluid to be analysed will pass, also passing through the first focus $F'_1$ and orthogonal to the axis A'. The holes 33 and 34 may also be orthogonal to each other.

A second part 35, for example made of aluminium, with a generally cylindrical and tubular shape, is screwed onto the outside of the first part 31 so as to prolong the cavity 32. It is used to house two lenses; a concave lens 36 and a convex lens 37 with shapes adapted to each other and arranged adjacent to each other. The optical centre of the group formed by the lenses 36 and 37 is coincident with the second focus $F'_2$. The optical axis of this group of lenses is also coincident with the axis of symmetry A'. A support element 38, screwed to the end of the second part 35, fixes the group of lenses into the optical device.

Figure 7:
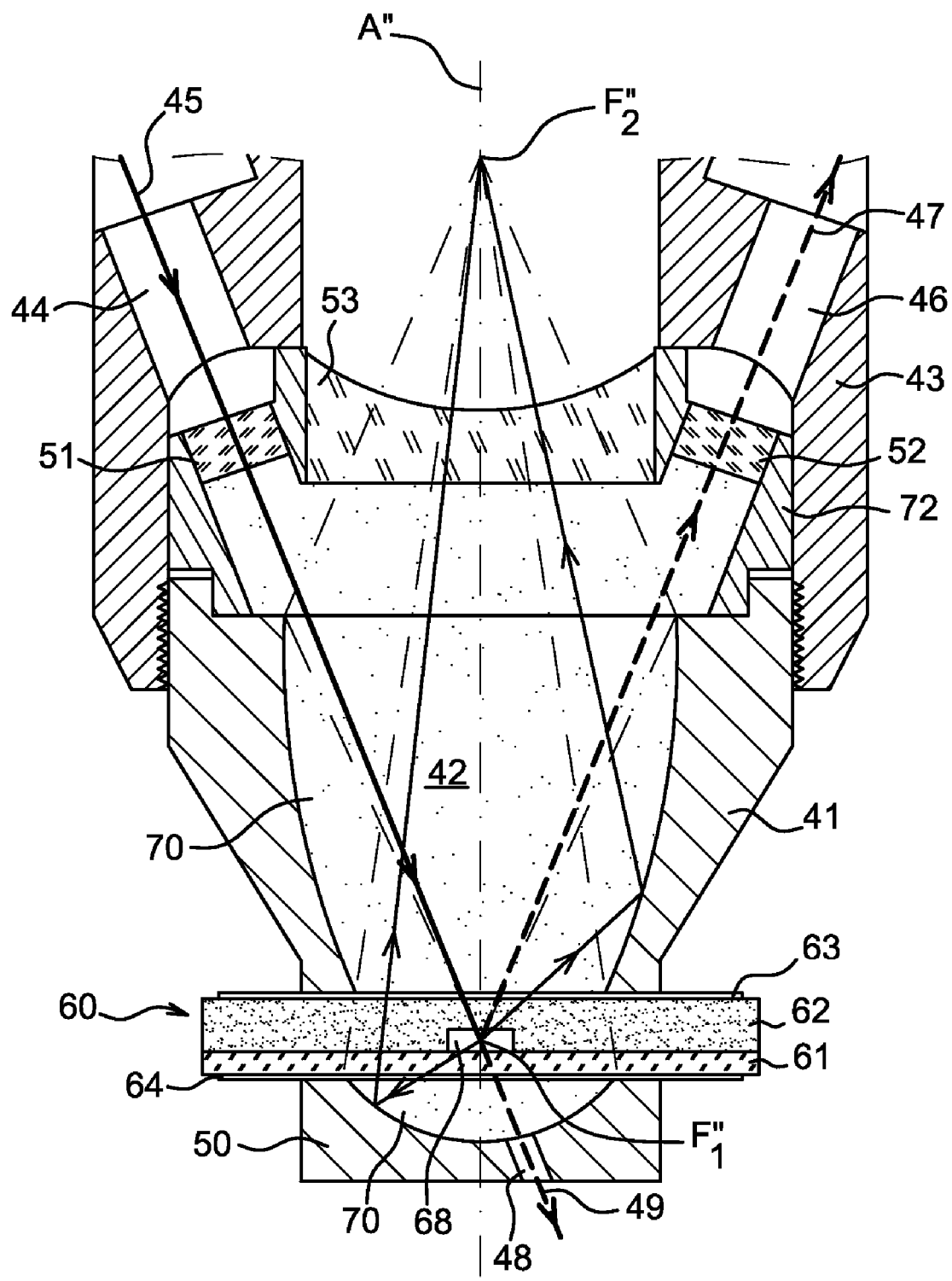
FIG. 7 is a longitudinal sectional view of another optical device according to this invention.

FIG. 7 is a longitudinal sectional view of another optical device according to this invention. The device comprises a first generally cylindrical part 41 for example made of aluminium, with an incomplete ellipsoid shaped cavity 42. The ellipsoid shape provides a first focus $F''_1$ and a second focus $F''_2$ on the axis of symmetry A''. The device comprises a second generally cylindrical part 72 superimposed on the first part 41, a third generally cylindrical part 43 that is screwed onto the first part 41 and is used to fix the second part 72, and a fourth cavity closing part 50.

Holes are drilled in the parts 72 and 43 providing an entry passage 44 for the excitation light beam 45 and an exit passage 46 for the reflected excitation light beam 47. The part 50 also has a hole 48 for the transmitted excitation light beam 49 to pass through.

The part 72 has transparent plugs 51 and 52 in the passages 44 and 46. The parts 72 and 43 have a central opening through which a concave lens 53 is installed closing off this central opening. The lens axis 53 is coincident with the axis A''. The lens 53 is concave towards the outside of the device. The focus of the lens 53 coincides with the second focus $F''_2$.

A support 60 of the medium containing the constituents to be analysed is arranged between the parts 41 and 50. The support 60 is transparent. For example, it includes a glass slide 61 covered by a silicone layer 62 in which a channel 68 is formed passing through the first focus $F''_1$. The support 60 includes a protection film 63, 64 on each of its main faces. The channel 68 carries the flow of a fluid to be analysed at the first focus $F''_1$.

The inside of the cavity, including the space between the support 60 and part 50, is filled with a transparent material 70 such as silicone so that there is no air layer along light paths emitted by the fluid to be analysed so as to avoid introducing a parasite refraction index.

The invention claimed is:

1. Optical device including a cavity for which at least part is ellipsoidal with a first focus and a second focus, the device including means of presenting a medium containing components to be analysed in the cavity at the first focus, the device also including means of transporting an excitation light beam in the cavity along a path also passing through the first focus to illuminate said medium at the first focus, said ellipsoidal part of the cavity (2, 32) including a wall reflecting light emitted by said medium in response to the excitation light beam, the device including means of collecting said emitted light at the second focus,
wherein the means used to present said medium are capable of making the medium circulate along a path passing through the first focus,
wherein the angle between the path of the means used to circulate the medium and the path of the means used to transport an excitation beam is less than 90° at the first focus, and
wherein the means used to circulate the medium include a transparent tube, at least at the first focus.

2. Optical device set forth in claim 1, wherein the path of the means used to circulate the medium and the path of the means used to transport an excitation beam are both perpendicular to an axis of an ellipsoid corresponding to the ellipsoidal shape of the cavity.

3. Optical device set forth in claim 1, wherein the means used to circulate the medium include an injector tube of the medium with one end located at the first focus and a collector tube of said medium with one end located at the other side of the first focus so that the medium is directly subjected to the excitation light beam.

4. Optical device set forth in claim 1, wherein the optical device is provided with orifices through which the tube or injector tube and the collector tube can pass.

5. Optical device set forth in claim 1, wherein the optical device is provided with an inlet orifice of the excitation light beam and an outlet orifice of the excitation light beam.

6. Optical device set forth in claim 1, wherein the means of presenting said medium include a case matching the shape of said part and wherein said medium can be housed at the first focus.

7. Optical device set forth in claim 6, wherein the case being transparent, the reflecting wall is the wall of said part.

8. Optical device set forth in claim 7, wherein the case is made of a material forming said reflecting wall.

9. Optical device set forth in claim 1, wherein the means of presenting said medium include a support including said medium and that can be inserted in the optical device to present said medium at the first focus.

10. Optical device set forth in claim 9, wherein the support includes at least one housing to contain said medium.

11. Optical device set forth in claim 9, wherein the support includes at least one channel internal to the support to transport said medium to the first focus, in a transparent part of the support.

12. Optical device set forth in claim 9, wherein said support is a lab on a chip.

13. Optical device set forth in claim 1, wherein the means of presenting said medium comprise a support provided in the cavity and supporting said medium so as to present said medium to the first focus.

14. Optical device set forth in claim 1, wherein the cavity is completely filled with a substance transparent to the excitation light beam and to said emitted light, the means for collecting emitted light comprising an opening provided with a concave lens concave towards the outside of the device, for which the focal point coincides with the second focus located outside the optical device, and the axis of which is the axis of the ellipsoid corresponding to the ellipsoidal shape, the emitted light thus not passing through any air layer before coming out of the concave lens.

15. Optical device set forth in claim 1, wherein the emitted light collection means include an opening to allow light collected at the second focus to pass through.

16. Optical device set forth in claim 1, wherein the emitted light collection means include an opening equipped with a lens or a group of lenses, the axis of which is the axis of the ellipsoid corresponding to the ellipsoidal shape and for which the focal point coincides with the second focus.

17. Optical device set forth in claim 16, wherein the lens or group of lenses is placed in a reception housing of the device and is fixed to the device by a support element.

18. Optical device set forth in claims 1, wherein the optical device consists of at least two assembled parts.

19. Optical device set forth in claim 1, wherein the optical device is made of a metallic material.

20. Optical device set forth in claim 19, wherein the metallic material absorbs light at the wavelength of the excitation light beam and reflects light at the wavelength of the emitted light.

21. Optical device set forth in claim 1, wherein the optical device is made of a plastic material, the reflecting wall of the cavity being formed of a metallic material.

* * * * *